United States Patent [19]

Huch

[11] 4,250,738
[45] Feb. 17, 1981

[54] METHOD AND APPARATUS FOR MEASURING CHARACTERISTICS OF SMALL QUANTITIES OF LIQUID DROPPED ONTO A THERMOSTATICALLY HEATED TRANSDUCER, UTILIZING A WARM-UP AND MEASUREMENT PROGRAM

[76] Inventor: Albert Huch, Kugelgasse 1, D-3550 Marburg, Fed. Rep. of Germany

[21] Appl. No.: 45,853

[22] Filed: Jun. 5, 1979

[30] Foreign Application Priority Data

Jun. 6, 1978 [DE] Fed. Rep. of Germany ....... 2824709

[51] Int. Cl.³ ............................................ G01N 25/02
[52] U.S. Cl. ..................................... 73/15.4; 73/61.3; 178/635
[58] Field of Search ................... 73/15.4, 61.3, 75, 76, 73/19; 128/635

[56] References Cited

U.S. PATENT DOCUMENTS

| | | | |
|---|---|---|---|
| 3,074,270 | 1/1963 | Rabb | 73/76 |
| 3,929,605 | 12/1975 | Lubbers | 128/635 |
| 3,998,212 | 12/1976 | Reichenberger | 128/635 |
| 4,165,633 | 8/1979 | Raisanen | 73/76 |

*Primary Examiner*—Donald O. Woodiel

*Attorney, Agent, or Firm*—Michael J. Striker

[57] ABSTRACT

A dish transducer unit comprising a dish-defining structure into which a drop of sample fluid is dropped for contact with the electrical or electrochemical transducer of the transducer, both the dish-defining structure and the transducer unit being thermostatically heated. The technician presses a button to initiate a timer, whereupon a transducer warm-up period begins, during which the meter connected to the transducer is maintained inoperative, to preclude readings. When the transducer warm-up period ends, the meter becomes operative so that the technician can calibrate. Prior to completion of a timed calibration period, the technician must drop the sample into the dish-defining structure, or else the timer stops and the thermostatic heating is discontinued. If the sample is timely dropped, a sample warm-up period follows, during which the sample is heated and the meter again inoperative, followed by a reading-taking interval during which the meter is again operative. Upon conclusion of the reading-taking interval the timer stops, switching off the thermostatic heating action, and can be restarted only if the technician again presses the start button.

11 Claims, 1 Drawing Figure

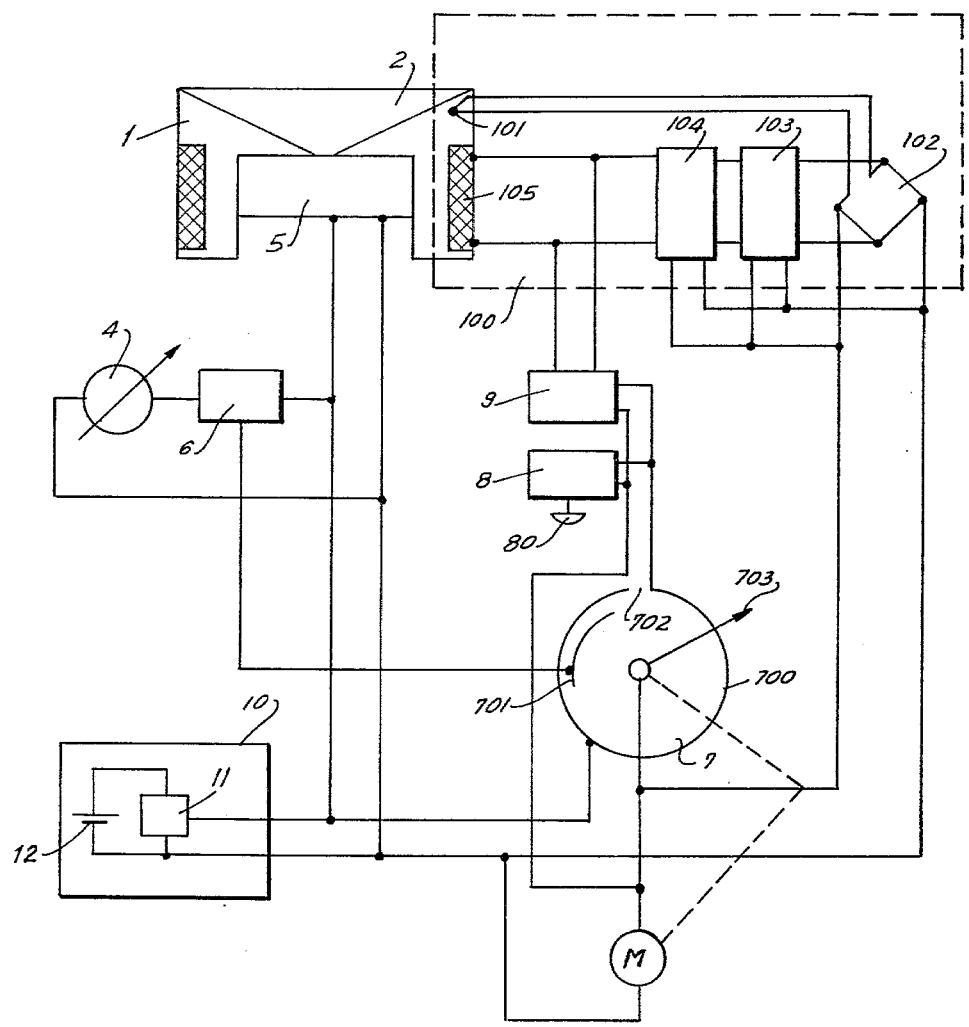

METHOD AND APPARATUS FOR MEASURING CHARACTERISTICS OF SMALL QUANTITIES OF LIQUID DROPPED ONTO A THERMOSTATICALLY HEATED TRANSDUCER, UTILIZING A WARM-UP AND MEASUREMENT PROGRAM

BACKGROUND OF THE INVENTION

The present invention concerns methods and apparatus involving the measurement of characteristics of a small quantity of fluid dropped into the little measuring dish or measuring pan of a dish transducer unit. The small quantity of fluid is dropped into the little dish of the transducer unit, and directly contacts the transducer of the unit immediately, or flows down the side of the little dish to the center of the dish, where it then makes physical contact with the transducer of the transducer unit. Such dish transducer units are thermostatically heated, both the transducer unit itself and the little dish or pan thereof, for operativeness and in order to bring the small quantity of fluid up to requisite temperature before actually performing the measurement for which the transducer is employed. One known transducer unit of this type employs a polarographic oxygen-concentration transducer and a drop of blood is dropped into the little dish of the transducer for a polarographic blood-oxygen concentration measurement. However, such dish transducer units are also employed to measure other properties and of other fluids.

Such dish transducer units are often portable and provided with their own battery. In that case, the factor of energy consumption becomes a significant problem, because considerable amounts of energy are required to bring the transducer of the unit and the dish of the unit up to operative temperature. Accordingly, after the transducer unit's thermostatic system has brought the transducer up to operative temperature, and thereafter continues to keep the transducer at operative temperature, delay in actual performance of the measurement involved can be very wasteful of energization. In order to minimize energy waste, the measurement should ideally be performed as soon as possible after the operative temperature has been reached. On the other hand, because the heating power of the transducer unit's battery may be rather low, a considerable length of time, e.g., more than a minute, may be required for the warm-up operation. If the user, because he becomes impatient from the desire to avoid heating-energy waste, or for other reasons, performs the measurement before the warm-up period is through, the result of the measurement may be highly inaccurate. Thus, these two factors tend to a certain extent, to contradict each other.

Furthermore, usually the drop of fluid placed into the little dish must itself be brought up to a certain temperature, before performing the measurement. This involves further delay before the measurement can be properly performed, and likewise if this heating, which is likewise thermostatically performed, is continued too long, heating-energy waste once more ensues.

These two problems, the time required to warm up the transducer and the time required to warm up the drop of fluid to be measured, are of identical character, but they represent two sources of difficulty, not one. Thus, for example, it is in general not appropriate merely to drop the drop of fluid into the dish of the transducer at the start of the warm-up of the transducer unit's transducer, i.e., in order to combine the two warm-up operations with respect to time. Instead, it is generally necessary first to bring the transducer up to operative temperature, before dropping in the drops of blood or the like, so that the meter of which the transducer unit forms a part can be adjusted or calibrated prior to the actual measurement. I.e., only after the transducer has been brought to operative temperature, and then the meter adjusted or calibrated, is the drop of blood, or the like, to be dropped in, and then the second warm-up period commences. With dish-type transducer units, e.g., incorporating a polarographic oxygen-concentration transducer, the meter involved may be very sensitive even to changes of ordinary atmospheric pressure, so that such readjustment or calibration may be necessary very often. For the same reason, after the first warm-up period and the subsequent adjustment or calibration is performed, the drop of blood or the like should be dropped in as soon as possible and the measurement performed, i.e., before the calibration can begin to grow stale.

SUMMARY OF THE INVENTION

Accordingly, it is a general object of the invention to provide a dish transducer unit of the type in question so designed that the various timing problems inherent in the performances of a measurement using such a transducer unit be automatically taken into account, in the operation of the transducer unit itself, and also to the extent necessary in the operation of the meter incorporating such transducer unit.

In accordance with a broad concept of the invention, after the thermostatic heater has been switched on to initiate the first or transducer warm-up period, an indication of the completion of the first warm-up period is provided, and after the drop of fluid has been dropped into the dish of the dish transducer unit an indication of the completion of the second warm-up period is provided.

This makes it possible to very optimally take into account the requirements of a particular use of such transducer unit and meter. For example, in the case of polarographic blood-gas concentration transducers, after a drop of 40 milliliters of blood has been dropped into the transducer-unit dish, on the order of 90 seconds may be required for the blood to come into thermal equilibrium with the transducer of the unit and for diffusion processes occurring relative to the transducer's polarization electrode to come into a state of equilibrium, if the cross-sectional area of the polarization electrode is very small. Furthermore, previous to dropping in the drop of blood, and after the transducer has been brought up to operative temperature, about 40 seconds may be required to readjust or calibrate the transducer or its meter in preparation for the measurement to be performed, e.g., to take into account local atmospheric pressure, or merely to readjust an improperly adjusted meter, and so forth. These two time intervals are more or less constant for a given application and meter, and they have nothing really to do with the actual measurement to be performed, i.e., they must be performed before the actual measurment is performed. By designing the transducer unit and its meter such that relevant indications, and/or manipulative constraints, are provided relative to these time intervals, it becomes possible to establish a definite and repeatable sequence of operations particularly matched to the requirements of the application involved.

For example, in the case of blood-oxygen concentration measurement using such a transducer unit, after the first or transducer warm-up period is completed, and after any calibration work needed is completed, the drop of blood should be dropped into the transducer unit's dish and brought up to operative temperature so that measurement can then be performed. This second or sample warm-up period is then advantageously initiated, in accordance with one concept of the invention, by some phenomenon associated with the preparation for the measurement.

In the preferred embodiment of the invention described herein, for example, the transducer or its meter is switched on, and the first or transducer warm-up period begins, this requiring about 90 seconds, so that the transducer and the little dish of the transducer unit be brought up to operative temperature preliminary to contact by a blood sample. During this first, 90-second warm-up period, the meter's indicator is inoperative; e.g., if an illuminated-digit digital indicator, the digits thereof are all dark. This gives the technician no choice but to wait for the first warm-up period to end.

Then, upon elapse of the initial 90-second warm-up period, the meter's indicator becomes operative, although a blood sample has not yet dropped in. This informs the technician, in the most direct possible way, that the meter is now available for the performance of any calibration or readjustment work required. An experienced technician requires less than about 40 seconds to perform such calibration work, and within such 40-second calibration period furthermore has time enough left to then drop in the blood sample, which the technician proceeds to do. If technician has dropped in the blood sample during the 40-second calibration period, usually towards the end of it, the thermostatic system of the transducer continues to operate, so that the blood sample be brought up to operative temperature. During the second or sample warm-up period, the indicator of the meter becomes inoperative again, to prevent the technician from even thinking of taking a reading during the second warm-up period. After elapse of the 90-second sample warm-up period, the meter's indicator becomes operative again, and the technician can take an oxygen-concentration (oxygen partial-pressure) reading.

Thus, during the first or transducer warm-up period, the technician is prevented from atempting to perform any calibration work prematurely. Upon elapse of the first warm-up period, because the meter's indicator now becomes operative, the technician is informed that it is time to calibrate and then drop in the blood sample. After the calibration period ends, because the meter's indicator is inoperative again during the second warm-up period, the technician is prevented from attempting to take a reading prematurely. Upon completion of the second warm-up period, the indicator becomes operative again, informing the technician that he should now take his reading, i.e., that the actual measurement period has begun.

Advantageously, in accordance with a further concept of the invention, the actual measurement period, likewise, is limited as to duration. This constrains the technician to take his reading as soon as possible after the second or sample warm-up period has concluded, although a reasonable amount of time is allotted to him for this purpose, and then the indicator becomes inoperative again, and the thermostatic heating system of the transducer unit, too, becomes inoperative. This serves to assure that the actual reading is taken timely, furthermore provides automatic shut-off of the heating system to preclude the possibility of its inadvertently being left on and cause battery dissipation, and in general minimizes the amount of heating power wastefully used and the amount of time which the technician spends in the performance of one measurement.

According to a further concept of the invention, the transition from the calibration period to the second or sample warm-up period does not occur unless the sample has been dropped into the transducer-unit dish during the calibration period. If the sample has not been dropped in by the end of the calibration period, the meter's indicator automatically becomes inoperative and, more importantly, the transducer's thermostatic system automatically switches off. Thus, an automatic switch-off action is provided in addition to that which occurs upon completion of the measurement; if, for whatever reason, the technician switches on, or switches on and then calibrates, but does not continue with the measurement, no possibility of indefinitely continued power consumption exists. Also, this additional automatic switch-off action constrains the technician to drop in the blood sample within a reasonable amount of time after completion of the first or transducer warm-up period.

The automatic switch-off in response to the absence of the sample within a resonable time period is advantageously implemented by relying upon the boost in heating power drawn by the transducer's thermostatic system when the unheated blood sample is dropped onto the transducer-unit dish. The meter is so designed that it automatically switches off at the end of the calibration period, unless prior to the end of the calibration period the power drawn by the thermostatic system has experienced a surge above and beyond the magnitude of the power fluctuations incident to steady-state operation of the thermostatic system.

In terms of implementation, the two cycles of operation (i.e., transducer warm-up period plus calibration period; and sample warm-up period plus reading period) can be realized by resort to a single, but twice performed cycle of operation. In that case, for example, each cycle of operation is constituted by 90 seconds during which the meter's indicator is kept inoperative (i.e., during the transducer warm-up period), plus 40 seconds during which the meter's indicator is kept operative (i.e., during the calibration period, and then later during the actual reading period), with each of these two 90+40-second cycles of operation terminating in automatic shut-off of the transducer's thermostatic system, the exception being that this one cycle of operation is reinitiated (i.e., at the end of the calibration period) if before its conclusion a blood sample has been dropped in. This double or repeated use of what is essentially a single cycle of operation can be advantageous and simple when certain modes of implementation are involved, e.g., because it reduces the number of timing stages needed for an electronic timer, or the number of timing contacts needed for an electromechanical timer, etc.

This latter concept, the double use of one cycle of operation, is advantageously implemented using a self-holding or self-locking action. When the one cycle of operation is initiated, e.g., by briefly pressing a button, self-locking action continues the cycle of operation to completion, whereupon the self-locking action terminates; but if the blood sample has meanwhile been dropped in, the self-locking action is once more established, so that one more cycle of operation occur, and at the end of the latter nothing is left to reestablish the self-locking action and initiate a cycle of operation. If, because of absence of the blood sample, the second cycle of operation is not timely initiated, later dropping in of the blood sample does not initiate the second or repeated cycle of operation, because the thermostatic system has meanwhile been switched off and therefore does not experience the surge of heating energy otherwise resulting from the sudden presence of the blood sample.

Advantageously, the meter's battery is provided with a dual-action regulator. A dual-action regulator is operative for furnishing a constant current or voltage by means of ordinary voltage or current regulation, but only so long as the source battery voltage is at a level sufficient to assure that the regulated level of voltage or current can be furnished, and if the source voltage drops below such value, the regulator does not attempt to furnish the regulated level but instead furnishes zero voltage or current. This is very advantageous in a meter system such as here contemplated, for the sake of accuracy in general, but especially inasmuch as the second or repeated cycle of operated is triggered by a surge of the power drawn by the transducer's heating system; it is accordingly important that the level of power drawn be an accurate reflection of the sudden presence of the sample in the transducer-unit dish.

If the meter's transducer per se happens to be of the high-impedance type, then the power drawn by it is anyway extremely low, in which case the only real threat of battery dissipation comes from the heating system. In this case, it is advantageous that the transducer be connected to the battery not through the intermediary of the timer unit of the meter, but instead more directly. In this way, the transducer can be maintained powered indefinitely, thereby achieving better measurement repeatability and shorter start-up times; in that event, a separate manual on-off switch for the transducer per se would suffice for the situation that the meter is not to be used for a very protracted period of time.

If use is made of a power source, e.g., a mercury battery, which exhibits a sharp voltage decrease towards the end of its useful life, then, for the case that the transducer per se is permitted to be battery-powered for indefinitely long periods of time in the way just mentioned, the dual-action regulator already referred to assures that the voltage applied to the transducer not be excessively low; this can be of importance for certain types of transducers.

Advantageously, the temperature sensor of the transducer's thermostatic system is an element of a bridge circuit. As well know, bridge circuits thusly employed are very stable against voltage fluctuations, temperature various and drift effects. This is particularly important when, as in the presently preferred embodiment, the dropping in of the sample is detected by monitoring the resultant sudden surge of power drawn by the thermostatic system of the transducer. The thermostatic system is preferably so designed that during normal-use steady-state operation the incidental fluctuations in the amount of power it draws be kept low enough that the surge in drawn power resulting when the sample is dropped in be at least twice, preferably on the order of ten times, such incidental steady-state fluctuations; the use of a temperature sensor which forms one element of a bridge circuit facilitates the establishment of this condition, without excessive cost for the thermostatic regulator.

The sample-produced surge in the power drawn by the thermostatic system is advantageously sensed by a threshold circuit stage connected to the thermostatic system's heating element. Advantageously, the threshold circuit stage is monostable, and responds to the sudden surge of drawn power by providing a sample-present signal whose duration is somewhat longer than the calibration period, or at least not greatly shorter than that. In this way, if the technician involved performs the calibration work very quickly, or if calibration work is not performed and the sample is dropped in early during the calibration period, the sample-present signal will still be in existence at the end of the calibration period, so that the sample warm-up period be reliably initiated and not missed.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The single FIGURE schematically depicts a preferred but merely exemplary embodiment of the present invention.

DESCRIPTION OF THE PREFERRED EMBODIMENTS

In the Figure, numeral 1 denotes the dish-defining structure of a dish transducer unit such as here in question. The dish-defining structure 1 is made of thermally conductive material and defines a dish 2 into which a few drops of a fluid sample, e.g., 40 microliters of blood or of water, is dropped; in principle the sample need not be a liquid. Numeral 5 denotes per se the transducer of the transducer unit. The transducer may be a pH transducer, a conductivity transducer, a gas-concentration transducer, and in the latter case a polarographic blood-oxygen concentration transducer, etc., depending upon the particular application involved. The purpose of a dish transducer unit such as here illustrated is to drop a very small sample into the dish 2, so that it fall into the central aperture of the dish and come into operative engagement with the upper measuring surface of the transducer 5 per se, for performance of an electrolytic and/or electrical measurement. For example, in the case of a conventional gas-concentration transducer, the transducer 5 would comprise a permeable membrane stretched flat across its upper face, with a layer of electrolyte confined beneath the permeable membrane, with the reference and measuring electrodes being confined in the insulating body of the transducer but at their upper ends in conductive engagement with the confined layer of electrolyte; such transducers will be familiar to persons skilled in the art.

A heating element 105, here a heating winding wound around the dish-defining structure 1 of the dish transducer unit, is employed to heat the transducer 5 per se to operative temperature and to heat the dish-defining structure 1, so that a measurement be performed with both the transducer per se and the sample dropped into the dish at the required temperature; that is what a dish transducer unit of the type here in question involves.

The temperature of the transducer unit is monitored by a temperature sensor 101, connected as one element of a bridge circuit 102. The transducer unit's thermostatic system as a whole is shown enclosed in the broken-line rectangle. Temperature-error signals which develop are applied from the output of bridge circuit 102 to the input of an amplifier stage 103, and from the latter to the input of a regulator or error-correcting stage 104. Regulator stage is mainly comprised of a power amplifier, but may, in conventional manner, additionally include circuitry for implementing an other than simple-linear reaction to the temperature error signal, for example. The output of regulator stage 104 is connected across heating element 105.

The meter's power supply 10 comprises a battery 12, here by way of example a mercury cell, across whose output is connected a dual-action regulator 11. Dual-action regulator 11 furnishes a regulated output so long as the voltage across battery 12 is sufficient to maintain the regulated level; if the battery voltage is lower than that, dual-action regulator 11 furnishes zero output. The output of power supply 10 is connected across the two electrodes of transducer 5, in the illustrated embodiment permanently; this is appropriate when a very high-impedance transducer is involved, because the power consumption of the transducer is negligible. An on-off switch can be provided, if despite negligible power consumption it is desired to be able to disconnect the transducer 5 from power, e.g., when the meter is to be stored away for a considerable time.

Numeral 4 denotes the meter's indicator. The indicator may be a moving-needle unit, an illuminated-digit digital unit, or the like. Indicator 4 is connected across the two electrodes of transducer 5 via a controllable electronic switch 6.

The output of power supply 10 is connected to the input to the transducer's thermostatic system through the intermediary of an electromechanical timer 7. Timer 7 comprises an arcuate, stationary electrical contact 700, forming something less than a complete closed circle and having an interruption at 702. Timer 7 comprises a further arcuate, stationary electrical contact 701 whose angular span is smaller than that of arcuate contact 700. The timer furthermore includes a rotating wiper contact 703 which is driven clockwise by a small drive motor M.

When rotating wiper contact 703 is at an angular position (such as the one illustrated) contacting stationary contact 703, this serves to connect the drive motor M directly across the two output terminals of power supply 10, so that motor M be energized and drive wiper contact 703 clockwise. When rotating wiper contact 703 turns clockwise relative to the position illustrated and additionally makes contact with arcuate contact 701, this connects the upper output terminal of power supply 10 to electronic switch unit 6, and thereby renders indicator 4 operative. When wiper contact 703 turns still further and reaches the interruption at 702, it loses electrical engagement with arcuate contact 700, motor M becomes deenergied, and wiper 703 then stays at this stop position. The lower output terminal of power supply 10 is connected to one terminal of motor M and to one input terminal of bridge circuit 102, the other terminal of motor M and the other input terminal of bridege circuit 102 being connected to the wiper. Accordingly, except when wiper 703 is at stop position 702, the thermostatic system of the transducer is switched on; when wiper 703 reaches the stop position 702 and stops there, the thermostatic system is switched off, i.e., no heating current is supplied to heating element 105.

When wiper 703 is at stop position 702, the only way to initiate energization of motor M is to activate a switch unit 8 by pressing a pushbutton 80, thereby initiating operation of electromechanical timer 7. After such initiation, once wiper contact 703 has again made engagement with contact 700, pushbutton 80 can be released, without discontinuance of a timing cycle.

Connected in parallel to start switch unit 8 is a monostable threshold circuit 9, likewise capable of maintaining motor M energized when wiper 703 is at stop position 702. The inputs of monostable threshold circuit 9 are connected across the terminals of heating winding 105, and monitor heating current directly. If the transducer's thermostatic system is in a steady-state condition, and a drop of fluid is dropped into dish 2, the resultant small surge in the heating power drawn by heating element 105 is sensed by circuit 9, and the latter produced an output signal which serves, like start swith unit 8, to connect motor M directly across the output terminals of power supply 10. The threshold voltage of circuit 9, and equivalently the thermostatic system itself, is so designed that the heating-power surge resulting from the sudden dropping of the sample into dish 2, and triggering circuit 9, be at least two, and preferably ten times as great as the incidental heating-power fluctuating occuring during steady-state operation of the thermostatic system. In response to the sudden heating-power surge, the monostable circuit 9 produces an output signal whose duration is somewhat longer than the time required for wiper contact 703 to move from one to the other end of arcuate contact 701.

Although both start switch unit 9 and monostable threshold circuit 9 serve to energize motor M when wiper contact 703 is at stop position 702, there is a difference in operation between the two units 8 and 9. In particular, start switch unit 8 can effect energization of motor M even when the transducer's thermostatic system is switched off, whereas switch unit 9, because it is responsive to the surge in heating power drawn by the thermostatic system, can only operate when the thermostatic system is already connected to power.

The illustrated meter arrangement operates as follows:

Initially, wiper 703 is at stop position 702, and both motor M and the thermostatic system are unenergized. The electrodes of transducer 5, however, are connected to power supply 10; as already stated, this improves long-term stability and repeatability for certain types of transducers, e.g., polarographic oxygen-concentration transducers.

The technician presses pushbutton 80, and start switch unit 8 effects energization of motor M. Wiper 703 commences to turn clockwise and moves out of stop position 702 into engagement with stationary contact 700. At this point, self-holding motor energization is achieved, and the technician can let go of pushbutton 80.

This is now the first or transducer warm-up period, and lasts, for example, 90 seconds, i.e., until wiper 703 eventually reaches contact 701. During this 90-second transducer warm-up period, the thermostatic system is energized, and the transducer 5 and the dish-defining structure 1 of the transducer unit are brought up to operating temperature. During this warm-up period, electronic switch unit 6 is non-conductive, and indicator 4 gives no reading. The technician has no choice but merely to wait.

Upon completion of the transducer warm-up period, the transducer has reached operative temperature, and wiper 703 makes engagement with contact 701, as a result of which switch unit 6 becomes conductive and indicator 4 begins to provide a reading. Wiper 703 remains in engagement with contact 701 for, e.g., 40 seconds. This constitutes the calibration period of the metering arrangement, during which the technician makes any necessary calibrations or fine adjustments; some such transducers are susceptaible even to changes in ambient atmospheric pressure, necessitating such recalibration or readjustment, e.g., simple nulling, rather often. During this 40-second calibration period, the thermostatic system remains energized, and operates at steady-state.

If, during this 40-second calibration period, the technician fails, besides his calibration work, to additionally drop in the sample, then when wiper 703 again reaches stop position 702 motor energization is simply discontinued. The indicator 4 will furthermore have been rendered inoperative. Accordingly, it will be necessary for the technician to once more press start pushbutton 8. If, after the timer has stopped in this way, the technician attempts to drop the sample into dish 2, monostable threshold circuit 9 is unable to initiate another timing cycle, because at such time the thermostatic system, to which state 9 responds, has already been disconnected.

In contrast, if during the 40-second calibration period, usually towards the end of it, the technician has in fact dropped in the sample, monostable threshold stage 9 will respond and produce an output signal serving to keep motor M energized as wiper 703 crosses stop position 702, and thereby initiate another 90+40 second timing cycle.

The first, 90-second-long phase of this second timing cycle constitutes the sample warm-up period, during which the sample is brought up to the requisite temperature, and during which the sample comes into equilibrium with the transducer. Indicator 4 provides no reading, and the technician must again merely wait.

After elapse of the 90-second sample warm-up period, wiper 703 once more reaches contact 701, indicator 4 becomes operative again, here again for a 40-second time interval, and now the technician takes his actual reading. At the end of the 40-second reading-taking interval, the wiper 703 once again reaches top position 702, and motor M becomes deenergized, the self-holding motor energization terminating. Indicator 4 becomes inoperative again, and the transducer's thermostatic system is disconnected from power.

As already stated, the monostable threshold circuit 9 responds to detection of the sample by affording a switching action whose duration is somewhat longer than that of the calibration and reading-taking intervals, here somewhat longer than 40 seconds. Thus, if the technician, perhaps because no calibration is required in a particular instance, drops in the sample right at the start of the calibration period, the switching action thereupon established by stage 9 will continue through the remainder of the calibration period, and then also somewhat longer, so that wiper 703 be able to cross stop position 702 and initiate the sample warm-up period.

It will be understood that each of the elements described above, or two or more together, may also find a useful application in other types of circuits and constructions differing from the types described above.

While the invention has been illustrated and described as embodied in a metering arrangement of a particular type, whose timer is electromechanical instead of electronic, and whose timing cycle is repeated once for a complete cycle of operation, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. A method of using an automatic meter which has a temperature-controlled sample dish for accommodating a sample dropped therein, when the sample dish includes a transducer which contacts the sample and can generate a reading in response thereto, comprising:
   turning on the meter;
   automatically turning on a temperature control to bring the sample dish to a desired temperature while preventing a reading from being generated;
   automatically waiting for a first predetermined interval of time until the sample dish has reached the desired temperature;
   automatically indicating that the first predetermined interval of time has elapsed by generating a reading;
   automatically waiting for a second predetermined interval of time during which a sample may be dropped into the sample dish and during which the meter may be calibrated;
   if a sample has been dropped into the sample dish, automatically waiting a third predetermined interval of time during which the sample is also brought to the desired temperature and during which reading generation is automatically prevented and subsequently generating a reading automatically; and
   if no sample has been dropped into the sample dish, automatically turning off the temperature control and preventing a reading from being generated.

2. The method defined by claim 1, wherein the predetermined intervals of time are established by an automatic timer having a self-holding operation, which operation terminates if no sample has been dropped into the sample dish during the second predetermined interval of time.

3. A meter, comprising:
   a transducer;
   a sample dish associated with the transducer and into which sample dish a sample may be dropped to come into contact with the transducer;
   a heater heating the sample dish and transducer when the heater is energized;
   a heater control cooperating with the heater to cause the sample dish and any sample dropped therein and transducer to be heated to a desired temperature;
   a display upon which a transducer-generated meter reading may be displayed;
   a timer connected to the heater control and the display, and operating in a manner that (a) after the timer has been turned on, the heater control is operated for a first predetermined interval of time during which the heater control heats the sample dish and transducer to the desired temperature, (b) after the first predetermined interval of time, the display is energized to allow meter calibration, (c) after display energization, the heater control is kept operating for a second predetermined interval of time, during which meter calibration may take place and during which a sample may be dropped into the sample dish, (d) after a sample has been dropped into the sample dish, the display is de-energized while the heater control is kept operating for a third predetermined interval of time during which the sample may be brought to the desired temperature, and (e) after the third predetermined interval of time, the display is energized to enable a meter reading to be displayed thereon; and a start switch connected to the timer for turning the time on.

4. The meter defined by claim 3, wherein the timer further operates in a manner that if no sample is dropped into the sample dish during the second predetermined interval of time, the heater control is switched off and the display is de-energized.

5. The meter defined by claim 4, wherein the timer further operates in a manner that if no sample is dropped into the sample dish during the second predetermined interval of time, the timer will be turned off.

6. The meter defined by claim 5, further including a sample detector connected to the timer and responsive to presence of a sample in the sample dish, the sample detector being connected to the heater and responding to a surge in power drawn thereby caused by presence of a sample to be heated.

7. The meter defined by claim 3, further including a portable power supply and a dual-action regulator connected thereto, the dual-action regulator energizing the meter with a constant supply voltage when the power supply delivers voltage greater than a predetermined minimum voltage and de-energizing the meter otherwise.

8. The meter defined by claim 7, wherein the transducer is always energized by the power supply and wherein such energization takes place independently of timer operation.

9. The meter defined by claim 3, wherein the heater control includes a temperature sensor responsive to transducer temperature, the temperature sensor constituting one element in a bridge circuit.

10. The meter defined by claim 6, wherein the surge in power to which the sample detector responds is at least twice any steady-state fluctuation in power drawn by the heater.

11. The meter defined by claim 10, wherein the sample detector responds to such surge in power by generating a signal for a duration which is greater than the second predetermined period of time.

* * * * *